United States Patent
Müller-Auffermann et al.

(10) Patent No.: US 11,286,452 B2
(45) Date of Patent: Mar. 29, 2022

(54) FERMENTATION TANK AND METHOD

(71) Applicant: KRONES AG, Neutraubling (DE)

(72) Inventors: Konrad Müller-Auffermann, Freising (DE); Severin Thomandl, Freising (DE)

(73) Assignee: KRONES AG, Neutraubling (DE)

( * ) Notice: Subject to any disclaimer, the term of this patent is extended or adjusted under 35 U.S.C. 154(b) by 338 days.

(21) Appl. No.: 15/765,022

(22) PCT Filed: Oct. 17, 2016

(86) PCT No.: PCT/EP2016/074885
§ 371 (c)(1),
(2) Date: Mar. 30, 2018

(87) PCT Pub. No.: WO2017/067885
PCT Pub. Date: Apr. 27, 2017

(65) Prior Publication Data
US 2018/0320124 A1      Nov. 8, 2018

(30) Foreign Application Priority Data
Oct. 19, 2015   (DE) .................... 10 2015 220 315.8

(51) Int. Cl.
*C12M 1/00*    (2006.01)
*B01F 5/10*    (2006.01)
*B01F 5/02*    (2006.01)

(52) U.S. Cl.
CPC .......... *C12M 23/40* (2013.01); *B01F 5/0206* (2013.01); *B01F 5/10* (2013.01); *C12M 23/58* (2013.01); *C12M 27/18* (2013.01); *C12M 29/18* (2013.01)

(58) Field of Classification Search
CPC ...... C12M 23/40; C12M 23/58; C12M 29/18; C12M 27/18; B01F 5/10; B01F 5/0206
See application file for complete search history.

(56) References Cited

U.S. PATENT DOCUMENTS

| | | | |
|---|---|---|---|
| 923,571 A | 6/1909 | Cambell | |
| 3,741,533 A * | 6/1973 | Winn, Jr. | ............... B01F 5/0057 366/136 |
| 3,962,042 A | 6/1976 | Malick | |

(Continued)

FOREIGN PATENT DOCUMENTS

| | | |
|---|---|---|
| CN | 102481495 A | 5/2012 |
| CN | 102597209 A | 7/2012 |

(Continued)

OTHER PUBLICATIONS

Machine Translation of DE 10 2009 026 366 A1 (Year: 2020).*

(Continued)

*Primary Examiner* — Michael L Hobbs
(74) *Attorney, Agent, or Firm* — Marshall, Gerstein & Borun LLP

(57) ABSTRACT

A fermentation tank having a first supply or discharge line with a first central opening arranged at the lower end of the fermentation tank for supplying or discharging a product. The fermentation tank also has a second and a third supply or discharge line, each with a centrally arranged opening for supplying or discharging a product, the three openings being arranged at different height levels. Also, a method of fermentation using the fermentation tank.

10 Claims, 17 Drawing Sheets

(56) References Cited

U.S. PATENT DOCUMENTS 4,296,882 A * 10/1981 Kobayashi ............ B04B 5/0442
366/219
5,660,977 A 8/1997 Flores-Cotera et al.

FOREIGN PATENT DOCUMENTS

| | | |
|---|---|---|
| CN | 203208926 U | 9/2013 |
| DE | 102009026366 A1 * | 2/2011 ............ C12M 23/58 |
| DE | 102012025027 A1 | 6/2014 |
| EP | 0250998 A2 | 1/1988 |
| GB | 1060722 A | 3/1967 |

OTHER PUBLICATIONS

International Search Report for Application No. PCT/EP2016/074885, dated Jan. 25, 2017.
European Examination Communication for Application No. 16782066.1, dated Nov. 25, 2020.
Notification of the First Office Action with Translation for Chinese Application No. 201680061383.0, dated Nov. 4, 2020.

* cited by examiner

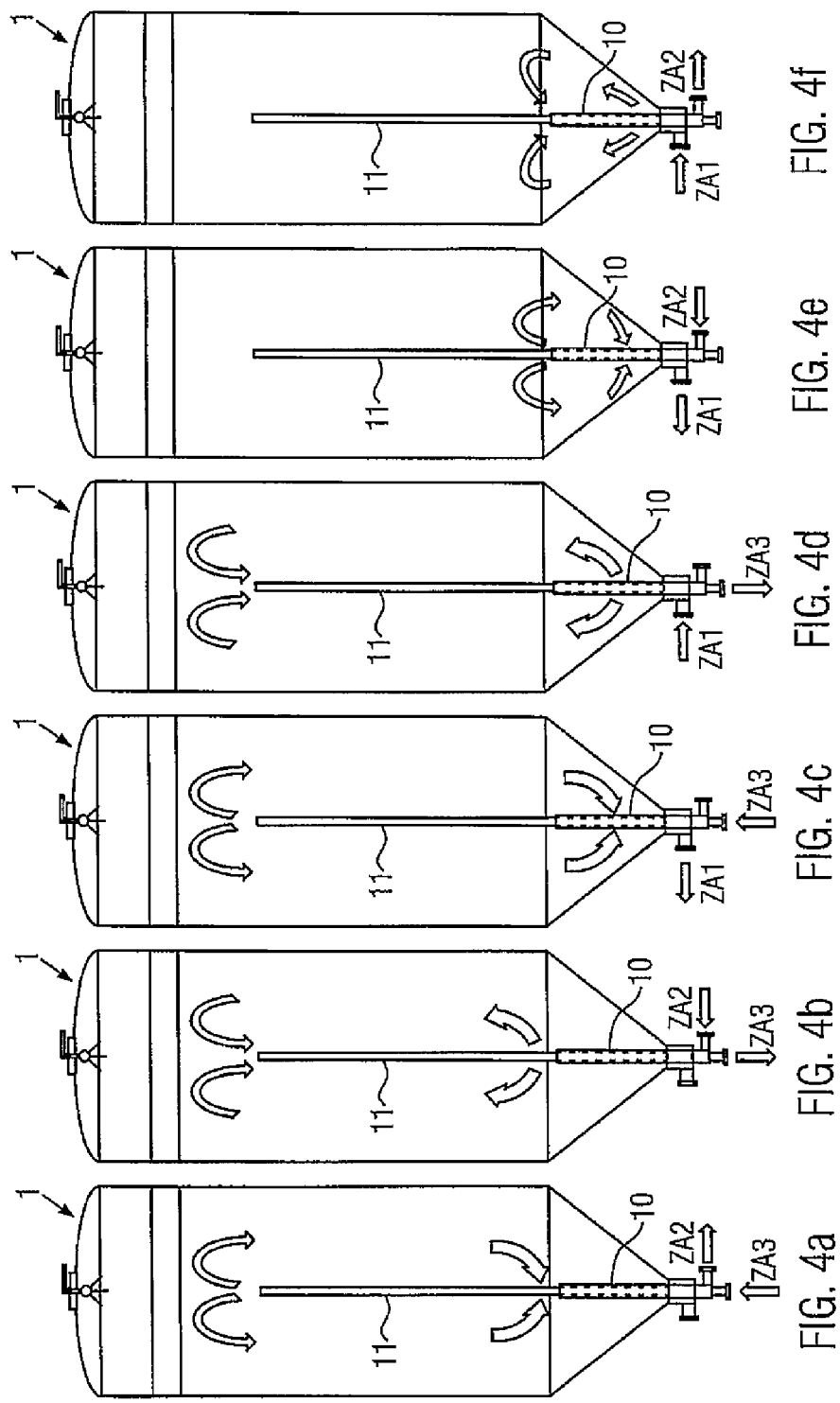

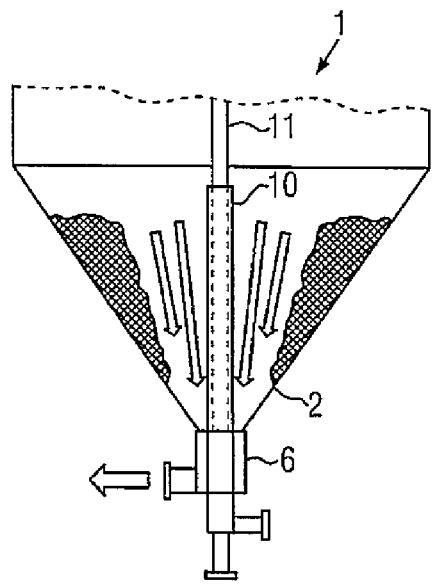
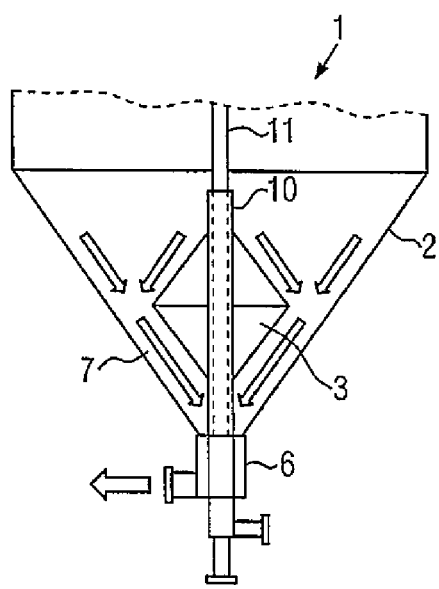
FIG. 6a  FIG. 6b
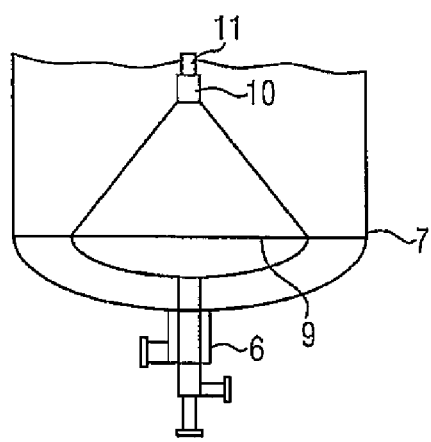
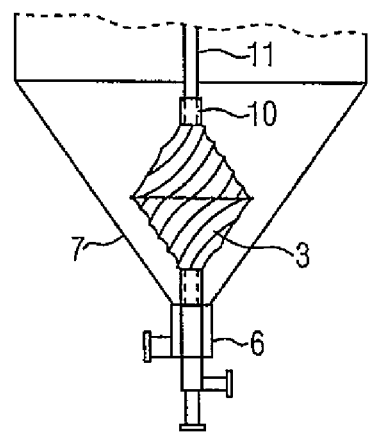
FIG. 7a  FIG. 7b

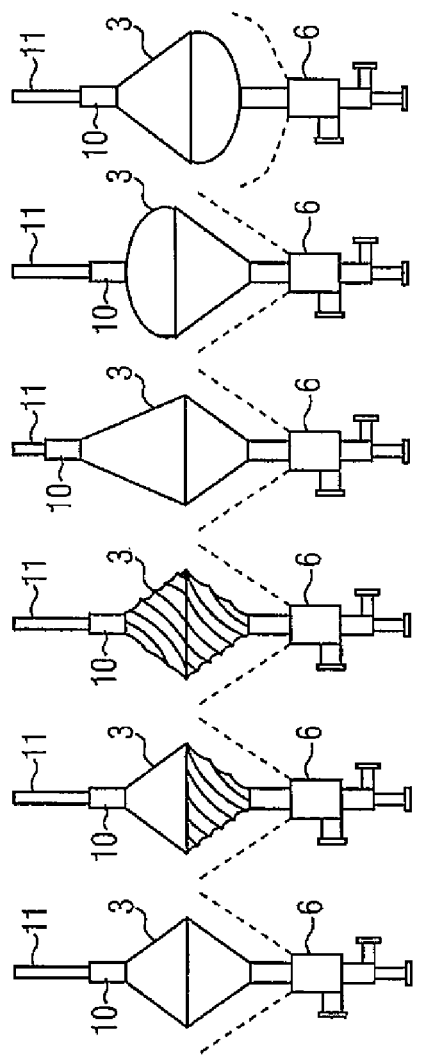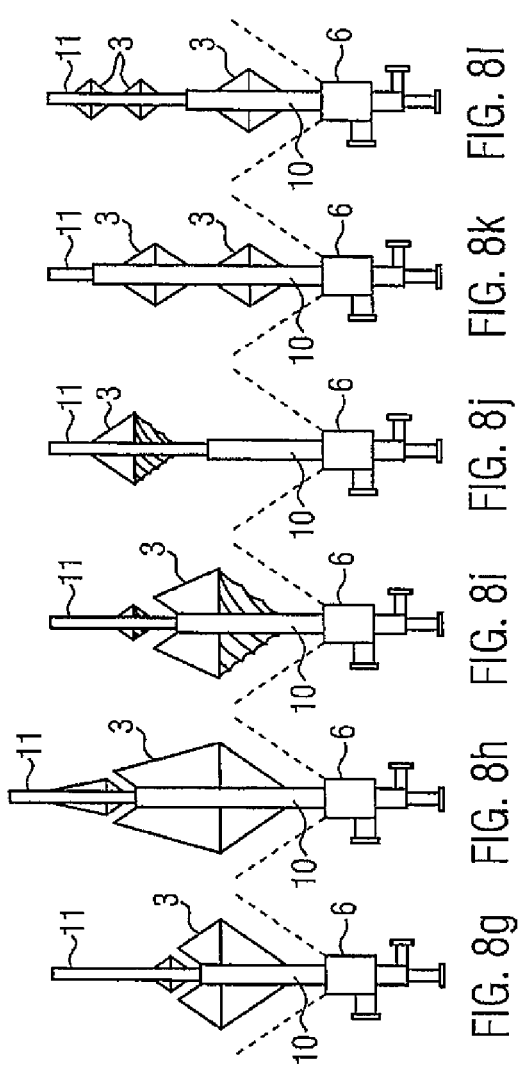

FERMENTATION TANK AND METHOD

CROSS-REFERENCE TO RELATED APPLICATION

The present applicaton is the U.S. national phase of Internaitonal PCT Application No. PCT/EP2016/074885, filed Oct. 17, 2016, which claims priority to Germany Application No. 10 2015 220 315.8, filed Oct. 19, 2015. The prioirity application DE 10 2015 220 315.8, is hereby incorporated by reference.

FIELD OF THE DISCLOSURE

The invention relates to a fermentation tank and a fermentation method.

BACKGROUND

Fermentation tanks and fermentation methods are already known from prior art. With fermentations, the inoculated substrate is commonly filled into the tanks from below. This is followed by the method steps of fermentation and storage, which typically take several days to weeks. The particles (for example hops, yeasts and trub), contained in the liquid or also added during these method steps, gradually sediment and accumulate in the lower region of the tank. Respective tanks have a filling opening at their lower end. It also serves to remove particles and subsequent fluid. With sediment extraction, care must be taken that this does not occur too quickly, otherwise there is a risk of channeling and thereby inefficient particle removal.

Stirring or circulation methods can further be implemented in order to accelerate the process of fermentation and thereby to render fermentation more efficient or to optimize separation processes. However, this prevents sedimentation. This in turn renders obsolete a more elaborate separate particle separation, e.g. by way of centrifuges, and leads to the reduction of method efficiency that is desired by circulation.

SUMMARY OF THE DISCLOSURE

Based on this, the object of the present invention is to provide an improved fermentation tank and an improved fermentation method which enable more efficient fermentation with simultaneous efficient sedimentation.

A fermentation tank is presently understood to be a tank that can be used as a fermentation and/or storage tank. The fermentation tank according to the invention comprises a central opening at its lower end with a first supply or discharge line. The supply or discharge line is a line that can be used both to supply a product as well as to discharge a product. A product is presently to mean e.g. wort laden with yeast, mash, beer, yeast sediment, hop sediments, protein deposits, gas, e.g. oxygen, nitrogen or air or steam and/or other multiphase fluids (sediment/fluid mixtures or sediment/fluid/gas mixtures). A respective opening at the lower end is mainly understood to be for loading the fermentation tank with product, presently, in particular, wort laden with yeast or beer or beer after primary fermentation. In addition to this first supply or discharge line according to the invention, a further second and third supply or discharge line are provided. The supply/discharge lines also each have a centrally disposed opening for the supplying or discharging product, where the three openings are arranged at different height levels. Central presently means in a center region of the fermentation tank.

The central arrangement of three possible supply and discharge lines entails the advantage that, e.g. two of the supply or discharge lines can advantageously be used for circulating product in the fermentation tank. Due to the central arrangement of the openings, it is possible that the flows in the reactor can form uniformly and symmetrically relative to the center axis. The sediments can therefore deposit homogeneously and be extracted better. Flow regions can be set variably. The flexible possibility of using all three lines, both as supply or discharge lines, in particular for circulation, further enables an ideal adaptation to different processes and process steps, i.e. e.g. ideal defibration and reaction catalysis. The arrangement according to the invention enables in particular, for example, that sediment formation takes place in the lower region of the fermentation tank and a circulation takes place simultaneously above between the openings in an upper level, so that the fermentation process as a whole can proceed in an accelerated manner.

With a variable flow reversal, the device can be operated ideally in circulation, optionally also with partial circulation (for example, if a sump is left in the tank).

The arrangement according to the invention further entails the advantage that a respective arrangement is very easy to clean. The central arrangement causes no spray shadows, especially during cleaning. A corresponding fermentation tank is also ideally employed for semi-continuous or continuous process management (where continuous can be understood to mean fully continuous).

According to a preferred embodiment, the first supply or discharge line can comprise a respective feed tube, which is preferably arranged outside the fermentation tank. According to a preferred embodiment, the second supply or discharge line comprises a second tube and the third supply or discharge line a third tube, which extend at least in sections within the fermentation tank.

Such a configuration is simple and inexpensive to implement.

Advantageously, the second and third tube are arranged within each other, preferably concentrically within each other, where the inner tube can extend beyond the outer tube. The inner tube, presently e.g. the third tube, therefore comprises the third opening at its end, while the area of the second opening corresponds to the inner cross-sectional area of the second tube minus the cross-sectional area of the inner tube and is at a correspondingly lower level. A corresponding arrangement is particularly clever and space-saving and is additionally easy to install and clean. Finally, a corresponding arrangement allows for particularly symmetrical and uniform flow formation. By using this tube-in-tube system, counter-current operation is also possible, so that heat transfer can additionally be improved.

According to a preferred embodiment, the second and the third tube protrude from below, in particular through the first opening, into the interior of the tank. Such an embodiment is particularly advantageous for the reason that the second and the third tube can be led through the already existing first opening, without additional holes in the tank being needed. The second and the third tube can be easily inserted into the tank from below and also retrofitted or replaced and/or modified in shape and length as desired.

According to a further embodiment, the second and the third tube can protrude from above into the interior of the tank, in particular through the upper side of the tank. Here as well, the advantage arises that no holes are needed in the side wall, in particular not in the conical and/or cylindrical portion of the fermentation tank. Also in this embodiment, the tube-in-tube arrangement can be easily inserted from above into the tank and possibly be retrofitted or replaced in a simple manner.

According to a further embodiment, the second tube can protrude into the interior of the tank from below, in particular through the first opening, and the third tube from above, in particular through the upper tank side. The advantages mentioned above arise here as well.

According to a preferred embodiment, a displacement member is arranged in the lower tank region and is preferably installed at the second and/or third tube. The lower region presently indicates a region, the cross-section of which decreases towards the first opening. This lower tank region is typically formed to be conical. But also cambered bases, i.e. dished bases or sphero-conical bases are possible.

The displacement member displaces a portion of the volume and serves as a flow breaker or flow guide when extracting and/or filling the product. On account of the displacement member according to the invention, the product no longer flows two-dimensionally but in a ring-shape around a ring-shaped channel about the displacement member when the product is discharged. The ring-shaped flow causes a flow optimization in that channeling is prevented. Yeast or sediment, respectively, can be better and more efficiently separated from the liquid. In addition, more uniform temperature control of the sediment arises, since a central core of the sediment can no longer heat up uncontrollably. Due to the displacement member, the sediment also has a larger contact surface to the liquid, so that also metabolism, transport and diffusion effects can be promoted. In addition, the flow during storage and/or extraction of gas, sediment and/or product can be influenced by the distance of the displacement member to the tank base and/or by the structuring of the displacement member and/or the tank inner side and active process influence can thus take place. The displacement member can be advantageously attached to the second and/or the third tube (also exchangeably), so that no additional attachment for the displacement member on the tank housing is necessary, which can save costs.

Advantageously, at least one lower part of the lower tank region is removable, can in particular be pivoted away and/or be flanged on and/or can be dismantled, e.g. be formed as a so-called pivot or flange cone. The supply/discharge lines are preferably attached to or integrated into this removable base part. Likewise, a displacement member possibly to be provided can then be attached e.g. to this part or at the second and/or third supply/discharge lines. The supply/discharge lines according to the invention can then be installed in a simple manner, possibly supplemented by a displacement member, and also be retrofitted in existing fermentation tanks, where the accessibility to the tank from below continues to be ensured since the displacement member easily be pivoted away or can be flanged on/be removable.

Advantageously, the height and/or the diameter and/or the cross-sectional shape of the second and/or the third tube can be changed. For this purpose, the second and the third tube are at least in partially exchangeable. It is therefore possible, for example, to withdraw the second and the third tube from the fermentation tank and to replace them with respectively different tubes which are adapted to a different process, whereby the height levels of the openings can also be adapted accordingly. However, it is also possible to replace and to exchange the second and/or the third tube at least in part by variable attachment elements (for example plug-in, screw, bayonet, flange and/or clamp connections) or to modify it in a method or product-related manner, respectively.

The fermentation tank advantageously comprises tubing with a valve arrangement which is configured such that a circulation between an opening at a middle level and an opening at a highest level is possible. A circulation can then take place between, for example, a third and a second opening, where sediment can deposit at the same time i.e., a central flow-calmed zone is created in the lower tank region in which the sediment can accumulate or remain intact. This is particularly useful if processes are to be accelerated and sediment is to be subsequently or simultaneously removed.

According to a further embodiment, circulation can take place between an opening at the highest level and an opening at the lowest level. Sediments are therefore either extracted from below and supplied into the upper tank region, or they are swirled up by transferring the liquid from the highest level to the lower tank region. This approach is particularly recommended where reactions such as separations or mass transfers between the sediment and the liquid are to be obtained.

According to a further embodiment, the tubing and valve arrangement is configured such that circulation takes place between an opening at a lowest level and an opening at a middle level. The circulation causes a flow-calmed zone to form in the upper tank region. Particles can then continue to sink down well there and the sediments in the lower tank region can be separated/loosened at the same time.

This makes it clear that the central arrangement of three possible supply or discharge lines entails a large variety of process options, where the flows and/or the flow rates can be ideally adapted to different process steps, thereby obtaining process optimization.

It is also possible for one or more flow guide devices to adjoin at the end region of the second and/or the third tube and/or above the second and/or the third tube, in particular at least one device from the following group: tube section expanding or tapering in cross-section, plate-shaped distributors, nozzle, Venturi nozzle, spray ball, jet cleaner, swirl element, displacement member, distributor elements, and/or a functional element. A functional element is presently to be understood. The flow can therefore be further influenced, e.g. be widened.

In addition to the shapes and configurations described, the surfaces of the tubes and/or the devices and/or the cone inner sides can be treated as desired and/or made of any materials. For example, roughening can cause condensation nuclei and a resulting local gas formation to selectively develop and that flows can be influenced. Furthermore, the static friction and therefore, for example, the slip and drain behavior can be influenced by surface treatments and/or the selection of appropriate materials. The device according to the invention and a respective connection device or attachment device can be manufactured, for example, by way of lathing, grinding, polishing, etc. or optionally by way of 3D printing and/or assembly can be effected by way of welding, screwing, and/or bonding methods etc.

According to a preferred embodiment, the tank or the valve/tubing system of the unit according to the invention is connected to at least one further tank, where, in particular, the first and/or the second and/or the third supply or discharge line of a first tank is connectable to the first and/or the second and/or the third supply or discharge line of a second tank.

According to a preferred embodiment, the fermentation tank is interconnected with at least one further fermentation tank, where the second and/or the third supply or discharge line is connectable to the second and/or the third supply or discharge line of a further tank. A corresponding arrangement is particularly advantageous for continuous process management. For example, product which is disposed above the sediment in a first tank can be conveyed via the second and/or the third supply or discharge line from the interior of the tank into a further tank, in particular also via the second and/or the third supply or discharge line of the further tank. Likewise, only the sediment can be transferred and can thus e.g. gradually be concentrated.

It is particularly advantageous to have the fermentation tank be connected to a dosage device, in particular hops dosage device, where media, e.g. hop, is added via at least one of the supply or discharge lines. An adjuvant and/or other raw, auxiliary, operating, and base materials can be supplied in a simple manner via the already existing three supply or discharge lines.

The fermentation method according to the invention can cause circulation of the product between two openings of the three supply or discharge lines.

The circulation advantageously takes place between the openings of the second and the third supply or discharge line, i.e. the two upper openings. The sediment in the lower region of the fermentation tank can then advantageously be discharged via the first supply or discharge line.

If several fermentation tanks are interconnected, product can be passed, for example, via the second and/or the third supply or discharge line via a second and/or third supply or discharge line of a downstream tank into the downstream tank. It is also possible to circulate the tank contents of a tank completely or partially and transfer a partial flow via a branch-off, i.e. in the circulation line, into a downstream and/or upstream tank.

The invention also relates to the use of the fermentation tank according to the invention for a continuous or semi-continuous fermentation process.

BRIEF DESCRIPTION OF THE DRAWINGS

The invention is further illustrated using the drawings below.

FIG. 4a illustrates a first circulation option for the fermentation tank according to the invention.

FIG. 4b illustrates a second circulation option for the fermentation tank according to the invention.

FIG. 4c illustrates a third circulation option for the fermentation tank according to the invention.

FIG. 4d illustrates a fourth circulation option for the fermentation tank according to the invention.

FIG. 4e illustrates a fifth circulation option for the fermentation tank according to the invention.

FIG. 4f illustrates a sixth circulation option for the fermentation tank according to the invention.

FIG. 6a very schematically illustrates the flow behavior in a fermentation tank without a displacement member.

FIG. 6b schematically illustrates the flow behavior in a fermentation tank with a displacement member, with an arrow between FIGS. 6a and 6b indicating to a reader that a comparison is to be made between the fermentation tank without a displacement member, as illustrated in FIG. 6a, and with a displacement member, as illustrated in FIG. 6b.

FIG. 7a schematically illustrates a partial view of one embodiment of a fermentation tank with a displacement member.

FIG. 7b schematically illustrates a partial view of another embodiment of a fermentation tank with a displacement member.

FIG. 8a is a partial view of a lower portion of a distribution tank, illustrating a first embodiment of a displacement member according to the present invention.

FIG. 8b is a partial view of a lower portion of a distribution tank, illustrating a second embodiment of a displacement member according to the present invention.

FIG. 8c is a partial view of a lower portion of a distribution tank, illustrating a third embodiment of a displacement member according to the present invention.

FIG. 8d is a partial view of a lower portion of a distribution tank, illustrating a fourth embodiment of a displacement member according to the present invention.

FIG. 8e is a partial view of a lower portion of a distribution tank, illustrating a fifth embodiment of a displacement member according to the present invention FIG. 8f is a partial view of a lower portion of a distribution tank, illustrating a sixth embodiment of a displacement member according to the present invention FIG. 8g is a partial view of a lower portion of a distribution tank, illustrating a seventh embodiment of a displacement member according to the present invention FIG. 8h is a partial view of a lower portion of a distribution tank, illustrating an eighth embodiment of a displacement member according to the present invention FIG. 8i is a partial view of a lower portion of a distribution tank, illustrating a ninth embodiment of a displacement member according to the present invention FIG. 8j is a partial view of a lower portion of a distribution tank, illustrating a tenth embodiment of a displacement member according to the present invention FIG. 8k is a partial view of a lower portion of a distribution tank, illustrating an eleventh embodiment of a displacement member according to the present invention FIG. 8l is a partial view of a lower portion of a distribution tank, illustrating a twelfth embodiment of a displacement member according to the present invention

DETAILED DESCRIPTION OF THE PREFERRED EMBODIMENTS

Figure 1:
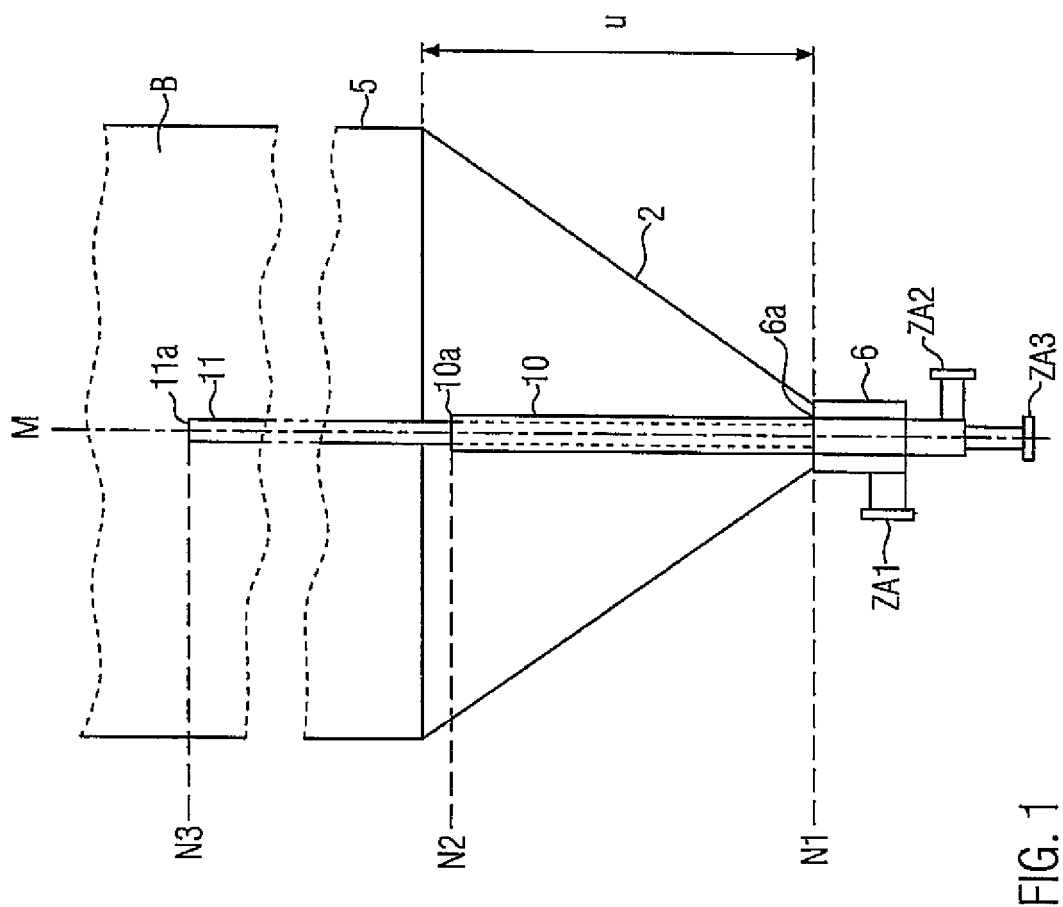
FIG. 1 very schematically shows a sectional view through one embodiment of a fermentation tank according to the present invention.

FIG. 1 very schematically shows a sectional view through a fermentation tank 1 according to the present invention. The fermentation tank can be e.g. a fermentation and/or storage tank for fermentation and/or maturation and/or storage and/or propagation/assimilation including all possible work steps such as the addition of organisms, hop, additives and/or other raw materials, adjuvants and working materials. The fermentation tank is there designed as a cylindroconical tank 1 with a cylindrical portion 5 and a conically shaped lower tank region 2. Section 3 tapering downwardly to an opening 6 does not necessarily have to be conical, but it is only essential that its cross-sectional area (viewed in cross-section perpendicular to the longitudinal axis L) reduces toward opening 6*a*. Lower tapered section 2 can be formed e.g. as a so-called cambered bottom or a dished bottom, respectively. In the case of a conical section 2, the cone angle β is at about 40-90°, preferably 60-90°. The height of a fermentation tank is e.g. in a range of 1.5 to 20 m The diameter m of cylindrical portion 5 is typically, e.g. 1 to 6 m. The height u of the tapering lower tank portion is e.g. 0.5 to 6 m.

Supply and/or discharge tube 6 connects at opening 6*a*. Although not shown, fermentation tank 1 is preferably supported by a plurality of feet or rings on the floor or, for example, mounted in a plate. The fermentation tank can also comprise a device for tempering, in particular, a cooling device, not shown, which cools the lower region at least in sections at the surface on the container wall. A respective tempering device can be provided also and/or exclusively in the cylindrical portion.

Figure 2:
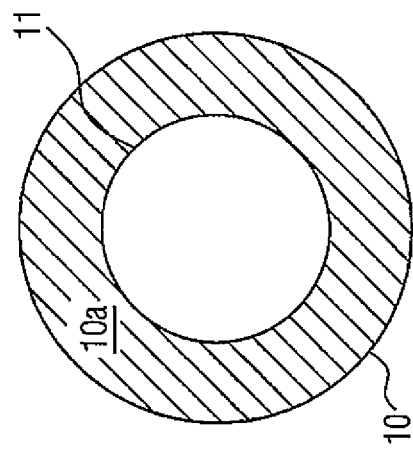
FIG. 2 shows a sectional view along the line I-I in FIG. 1.

According to the present invention, in addition to first supply or discharge line 6 for supplying or discharging product, fermentation tank 1 now comprises a second supply or discharge line 10 and a third supply or discharge line 11, each with a centrally arranged opening 10*a*, 11*a* for supplying or discharging product, where the three openings are arranged at different height levels $N_1$, $N_2$, $N_3$. Supply or discharge lines 6, 10, 11 comprise corresponding ports ZA1, ZA2, ZA3, which can be connected to a corresponding tubing system such that a respective product can be supplied or discharged and/or circulated in the circulation and can optionally be additionally or exclusively tempered there as well. The second and the third supply or discharge line comprises corresponding tubes 10, 11 which are arranged one inside the other, preferably concentrically within each other, where inner tube 11 should project beyond the upper edge of outer tube 10 and extend up to level $N_3$. The second opening of second supply or discharge line 10 is shown, for example, in FIG. 2. It results from the inner cross-sectional area of tube 10 minus the total cross-sectional area of tube 11 and is shown hatched in FIG. 2. Product can flow in second supply or discharge line 10 between tube 10 and tube 11. In this particular embodiment, the tube-in-tube system is passed through lower first opening 6*a*. No separate hole in fermentation tank 1 is therefore necessary, which is particularly advantageous. The effective first opening 6*a* then results from the cross-sectional area of the opening 6*a* minus the total cross-sectional area of tube 10. A ring-shaped opening, i.e. a ring-shaped flow channel arises both for opening 6*a* and opening 10*a* through which product can flow in and out, which is particularly advantageous for a symmetrical and uniform flow. The central arrangement of the openings or of tubes 6, 10, 11, respectively, in particular the concentric arrangement, has the advantage that the three supply or discharge lines can be integrated in a simple manner into the smallest possible space in the fermentation tank.

Figure 3D:
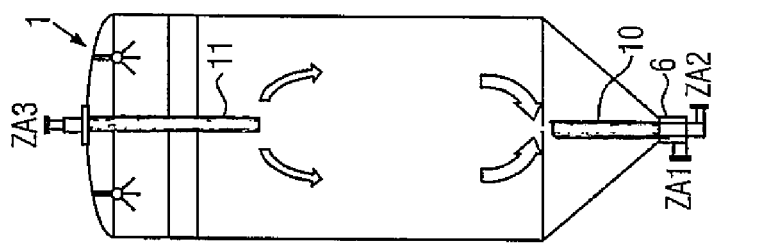
FIG. 3d schematically illustrates a fermentation tank with second and third supply or discharge lines at a third location.
Figure 3C:
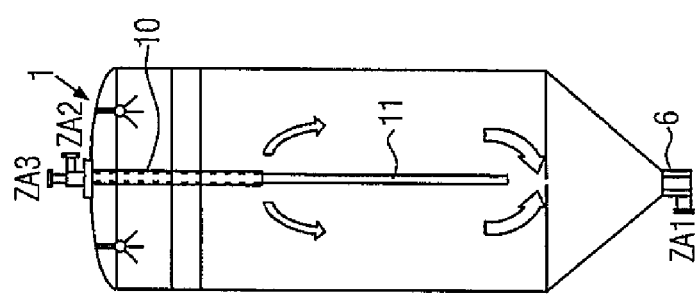
FIG. 3c schematically illustrates a fermentation tank with second and third supply or discharge lines at a third location.
Figure 3B:
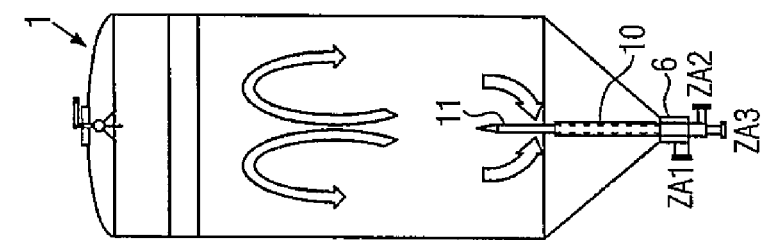
FIG. 3b schematically illustrates a fermentation tank with second and third supply or discharge lines at a second location.
Figure 3A:
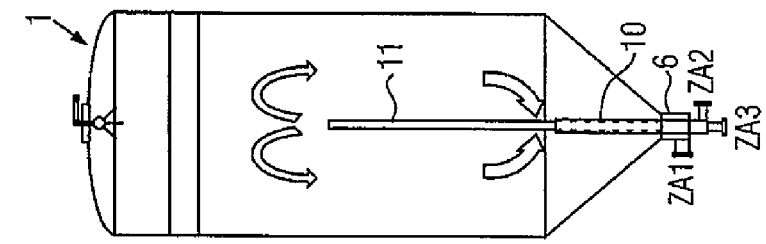
FIG. 3a schematically illustrates a fermentation tank with second and third supply or discharge lines arranged at a first location.

FIGS. 3*a-d* show further embodiments according to the present invention adjacent to each other. FIG. 3*a* corresponds substantially to the embodiment as shown in FIG. 1. The arrows represent a circulation of the product, where product is passed via third supply or discharge line 11 into fermentation tank 1 through opening 11a and is discharged through opening 10a via tube 10 and then again supplied via tube 11 to the circulation, while at the same time sediment can deposit in lower region 2 of fermentation tank 1. FIG. 3b shows an arrangement corresponding to that in FIG. 3a, only with relatively shorter tubes, where, as shall be explained later, the upper end of third tube 11 is formed as a nozzle. Tube 11 can optionally be kept shorter and a respective flow profile nevertheless forms in fermentation tank 1.

FIG. 3c shows another possible embodiment according to the present invention. Second and third tube 10, 11 there protrude from above into the interior of the tank, presently through the upper wall or a lid of the tank. Third tube 11 then extends through tube 10 and projects beyond tube 10, where the product, for circulating, flows in circulation out from opening 10a into the fermentation tank to opening 11a. Such a tube-in-tube design is also easy to attach in the fermentation tank.

FIG. 3d shows a further embodiment, in which second tube 10 projects into the interior of the tank from below, in particular through first opening 6a, and third tube 11 projects from above through the upper tank side into the interior of the tank, such that a flow can form for circulation between opening 11a and 10a. Such an arrangement is also easy to manufacture.

Figure 5:
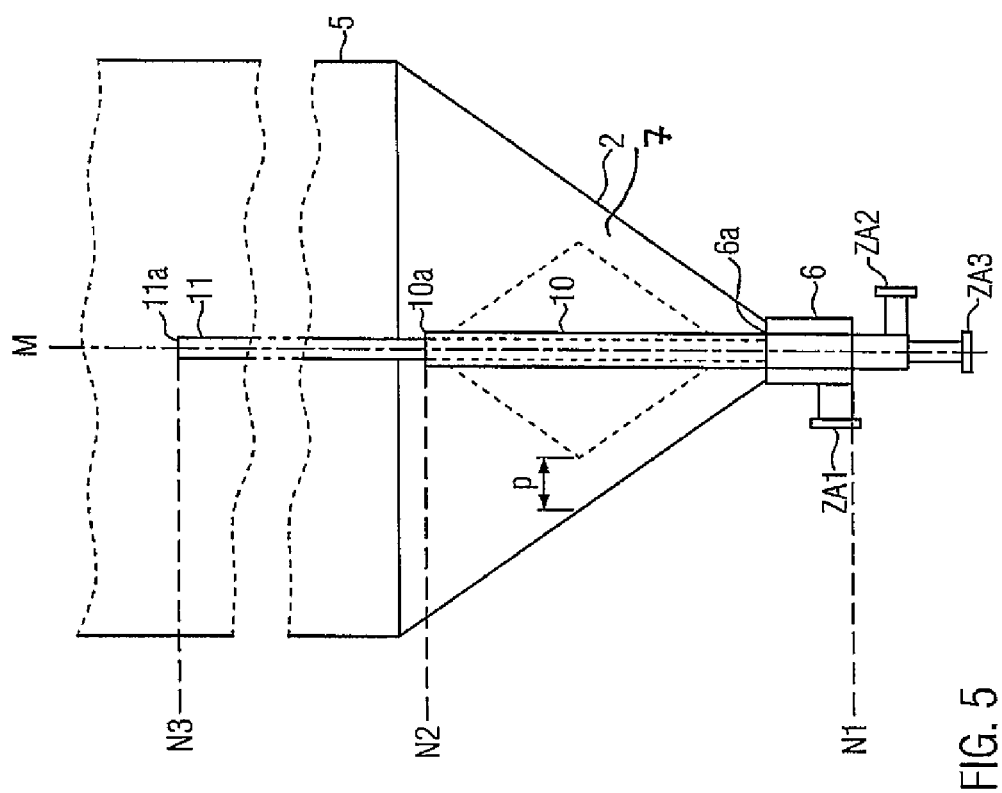
FIG. 5 very schematically shows a partial sectional view through a further embodiment of a fermentation tank according to the present invention with a displacement member installed.
Figures 9A, 9B, 9C, 9D:
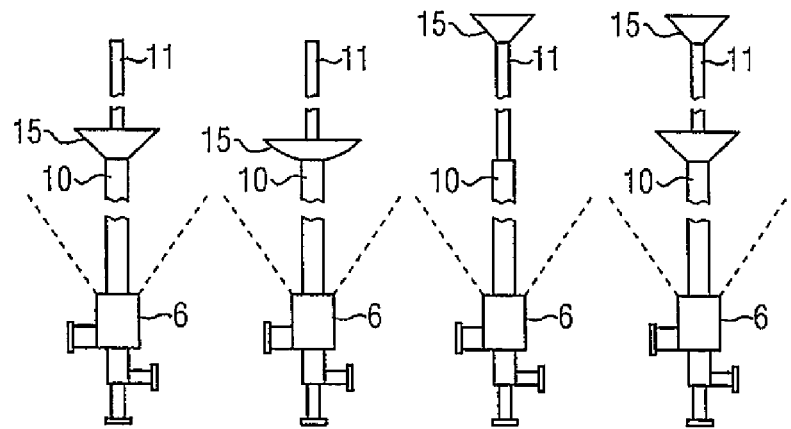
FIG. 9a shows a first version of a device for flow guidance arranged on the second and/or the third supply or discharge line.
FIG. 9b shows a second version of a device for flow guidance arranged on the second and/or third supply line or discharge line.
FIG. 9c shows a third version of a device for flow guidance arranged on the second and/or third supply line or discharge line.
FIG. 9*d* shows a fourth version of a device for flow guidance arranged on the second and/or third supply line or discharge line.
Figures 10A, 10B, 10C, 10D:
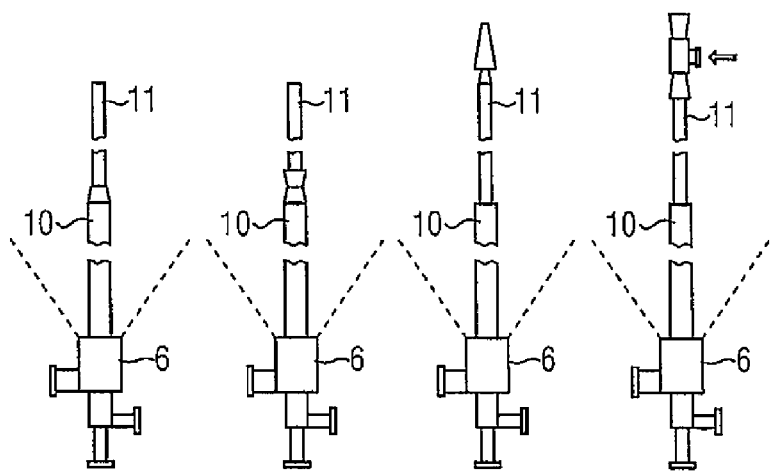
FIG. 10*a* shows a fifth version of a device for flow guidance arranged on the second and/or the third supply or discharge line.
FIG. 10*b* shows a sixth version of a device for flow guidance arranged on the second and/or third supply or discharge line
FIG. 10*c* shows a seventh version of a device for flow guidance arranged on the second and/or third supply or discharge line
FIG. 10*d* shows an eighth version of a device for flow guidance arranged on the second and/or third supply or discharge line
Figures 11A, 11B, 11C, 11D:
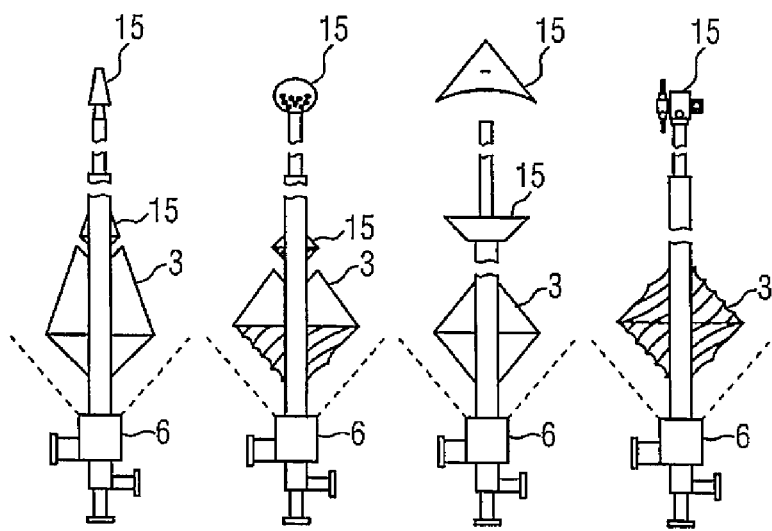
FIG. 11*a* shows a first combination of displacement members and devices for flow guidance.
FIG. 11*b* shows a second combination of displacement members and devices for flow guidance.
FIG. 11*c* shows a third combination of displacement members and devices for flow guidance.
FIG. 11*d* shows a fourth combination of displacement members and devices for flow guidance.
Figures 12A, 12B, 12C, 12D:
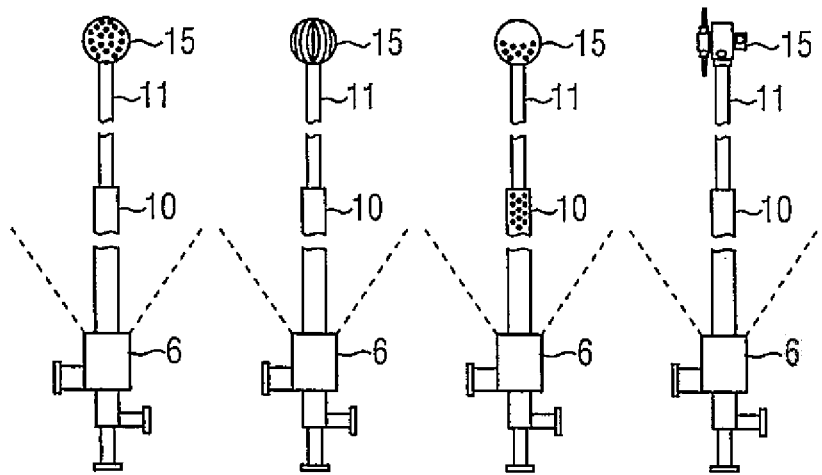
FIG. 12*a* shows a first version of a device for flow guidance arranged on the second and/or the third supply or discharge line.
FIG. 12*b* shows a second version of a device for flow guidance arranged on the second and/or third supply or discharge line.
FIG. 12*c* shows a third version of a device for flow guidance arranged on the second and/or third supply or discharge line.
FIG. 12*d* shows a fourth version of a device for flow guidance arranged on the second and/or third supply or discharge line.
Figures 13A, 13B, 13C, 13D:
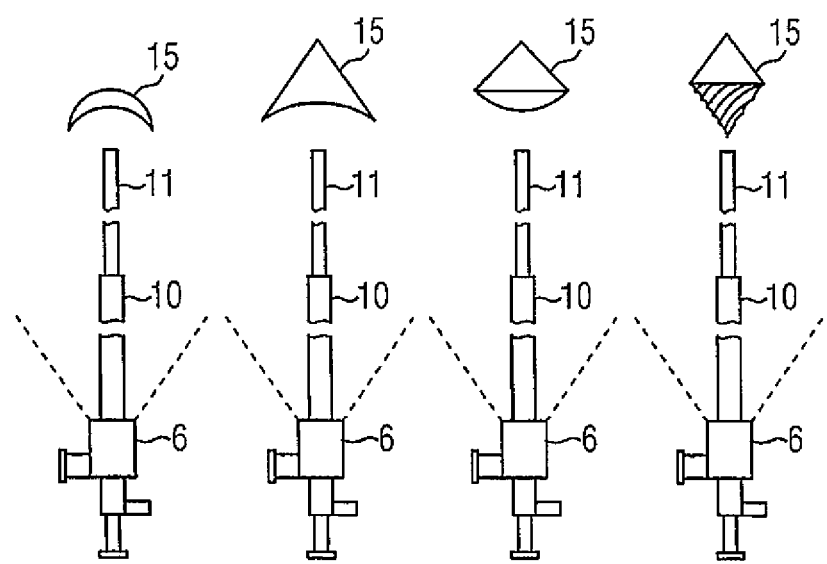
FIG. 13*a* is a partial view of a distribution tank that schematically shows a first device for flow guidance.
FIG. 13*b* is a partial view of a distribution tank that schematically shows a second device for flow guidance.
FIG. 13*c* is a partial view of a distribution tank that schematically shows a third device for flow guidance.
FIG. 13*d* is a partial view of a distribution tank that schematically shows a fourth device for flow guidance.

According to a preferred embodiment, a displacement member 3 is arranged in fermentation tank 1 and is preferably installed at second and/or third tube 10, 11. In FIG. 5, displacement member 3 is attached to the outer side of tube 10. Displacement member 3 is arranged in the lower region 2 of fermentation tank 1. Displacement member 3 is, for example, a closed member formed from stainless steel. The displacement member is designed and arranged such that a ring-shaped discharge channel 7 arises which opens into outlet opening 6a, where the diameter of the displacement member in a direction perpendicular to center axis M is greater than the diameter of first and or second tubes 10, 11. Displacement member 3 is arranged axially relative to opening 6a and center axis M, respectively, and formed, for example, as a double cone. The lower cone surface runs substantially parallel to the tank inner surface.

As can be seen in particular from FIG. 6a, b, channeling in the sediment, which arises, for example, at high outflow rates of the product and is illustrated in FIG. 6a, can be prevented by displacement member 3. The shape of displacement member 3 can be modified individually. As is evident from FIG. 7a, b, the shape can be adapted to the tank geometry or base geometry, respectively, and/or the flow can be specifically directed/influenced by the latter's shape. FIG. 8 shows several possible shapes of displacement members. Also several displacement members can optionally be attached to one and/or several supply or discharge lines and combined in a variable manner. FIG. 8a shows a double cone, 8b a double cone whose lower region is formed as a swirl element and causes the fluid flowing past to perform a rotational motion. FIG. 8c shows a double cone, where both the upper and the lower half are formed as a swirl element. FIG. 8d shows an asymmetrical double cone. FIG. 8e shows a swirl member which tapers in the lower region and is rounded at the top. FIG. 8f shows a displacement member with an upper tapered portion and a rounded portion at the bottom. FIGS. 8g-l show combinations of the elements shown in FIGS. 8a-f. The integrated displacement member can optionally be designed functionally, for example, in that tempering devices and/or gas/fluid flows are possible.

According to the invention it is also possible that the device further comprises a device 15 for flow guidance which either adjoins the second and/or the third tube or is arranged above the second and/or the third tube. A respective device 15 comprises, for example, a device from the following group: a tube section 15 expanding or tapering in cross-section, plate-shaped distributors or other distribution members 15, (see FIGS. 9a-d), nozzles, Venturi nozzles (see FIGS. 10a-d), spray balls, jet cleaners (see FIGS. 12a-d), and combinations thereof (see FIGS. 11a-d). It is also possible to arrange devices for flow guidance, such as flow members, baffles and distributor plates above the second and/or the third tube, as shown in particular in FIGS. 13a-d. It is particularly advantageous if the height and/or the diameter and/or the cross-sectional shape of the second and/or third tube are variable, where the second and/or the third tube are at least in sections exchangeable.

It is possible, e.g. to withdraw the second and/or third tube from fermentation tank 1 and to replace them with respectively different tubes and/or other, optionally functional elements which can be adapted accordingly. The second and/or third tube can be detachably attached to the tank with attachment elements (such as plug-in, screw, bayonet, flange and/or clamp connections). However, it is also possible to replace and to change the second and/or the third tube at least in part by way of variable connecting elements (for example plug-in, screw, bayonet, flange and/or clamp connections). But also the additional elements, such as displacement member 3 or the devices for flow guidance, can be attached exchangeably by way of respective connection elements, and/or be modularly expanded or changed, respectively.

Figure 14:
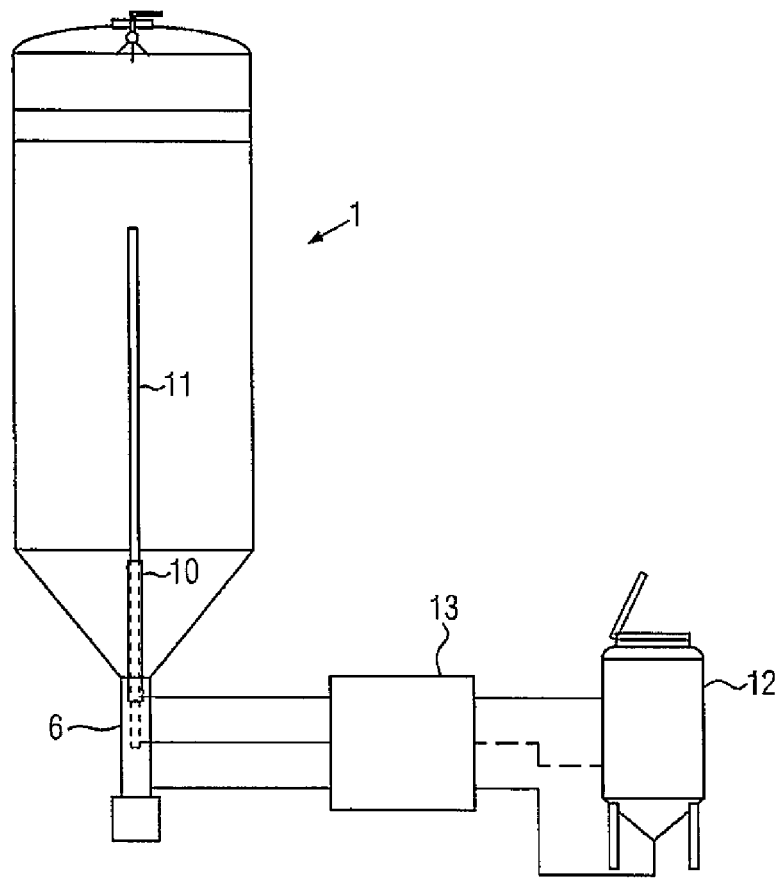
FIG. 14 very schematically shows a fermentation tank with a dosage device.

According to a preferred embodiment, as shown in FIG. 14, tank 1 can be provided with a dosage device e.g. hops dosage device 12, where medium, presently hops, can be added via at least one of supply or discharge lines 6, 10, 11. A corresponding supply or discharge line can be selected from the three supply or discharge lines via a corresponding valve arrangement 13, e.g. a valve manifold and/or a different type of port or interconnection and/or type of connection. No additional supply line must then be integrated into the system, in particular into the fermentation tank. Although FIG. 14 does not show any PBE (process-influencing unit), it can be contained optionally and/or in addition to the addition and/or removal of substances.

The medium to be added, for example hops products (such as hop pellets, hop extract, hop oils and/or hop umbels) is introduced into the optionally mobile or stationarily installed dosage tank of dosage device 12 The dosage tank is tightly closed. This is followed by the removal of air, for example by displacement with an inert gas and/or carbon dioxide. The container is then in part or entirely filled with the solution medium (e.g., beer and/or water), e.g. via one of three centrally arranged supply or discharge lines 10, 11, 6, preferably the second and/or the third discharge line, which are disposed above the sediment. Optionally, homogenization/dispersion can take place in the dosage tank. The mixture can be passed subsequently or at the same time through at least one of the supply or discharge lines into fermentation tank 1, in which the fermentation tank contents, i.e. the product, can be circulated, as shall be explained in more detail below. Furthermore, circulations can also or exclusively be performed via dosage tank 12, which can optionally also be equipped with separation devices, such as sieves and/or press screws. After the desired separation or extraction, the sediment can be ideally removed according to the invention or retained in the dosage tank and/or optionally further processed.

As can be seen, in particular, in FIG. 4 and also in FIG. 5, according to the fermentation method of the invention, it is possible to perform a circulation between two of the three openings 6a, 10a, 11a.

For this purpose, fermentation tank 1 comprises tubing with corresponding valves that are configured such that circulation is possible between one opening 10a on the middle level $N_2$ and one opening 11a at the highest level $N_3$, as shown in particular in FIGS. 4a and 4b. A circulation can then take place between, for example, a third 11a and a second 10a opening, where sediment can deposit at the same time i.e., a central flow-calmed zone arises in the lower tank region in which the sediment can accumulate or remain intact. The process can be accelerated in this manner. In FIG. 4a, port ZA1 is configured as an inlet and port ZA2 as an outlet. It is also possible to select port ZA2 as the inlet and port ZA3 as the outlet, as shown in FIG. 4b.

Figure 15:
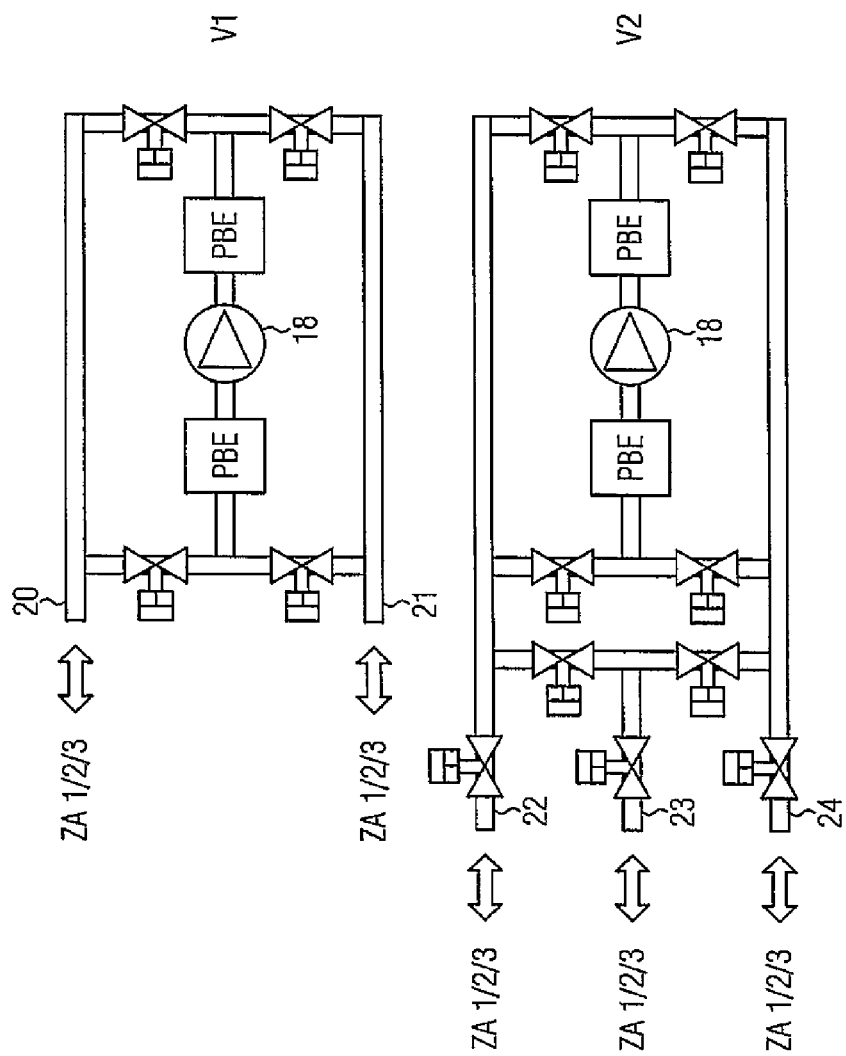
FIG. 15 very schematically shows two tubing variants, each for a fermentation tank according to the present invention.

It is also possible to switch the valves in the tubing, e.g. V1 or V2, as indicated in FIG. 15, such that a circulation can take place between an opening 11a at the highest level $N_3$ and an opening 6a at the lowest level $N_1$, as shown in FIGS. 4c and 4d, where FIG. 4c depicts port ZA3 formed as an inlet and port ZA1 as an outlet and FIG. 4d depicts port ZA1 formed as an inlet and port ZA3 as an outlet. Sediments are therefore either extracted from below and supplied into the upper tank region, or they are swirled up in that e.g. liquid is transferred from the highest level to the lower tank region. This approach is particularly recommended where reactions such as solutions or mass transfers between the sediment and the liquid are to be obtained.

Valve manifold V1 or V2, presently shown only as an example, can also be connected such that a circulation takes place between an opening 6a at the lowest level $N_1$ and an opening 10a at the middle level $N_2$. The circulation causes a flow-calmed zone to form in the upper tank region. Particles can therefore continue to sink down well there and solution/loosening of the sediments in the lower tank can take place at the same time, as shown for example in FIGS. 4e and 4f, where port ZA1 is used in FIG. 4e as an outlet and port ZA2 as an inlet, and vice versa in FIG. 4f.

The valve arrangements or tubing V1, V2 shown in FIG. 15 are only by way of example. A preferred variant provides for the use of at least 4-7 valves and one pump 18 so that e.g. flow reversals and the previously described methods for process and cleaning optimization are possible. The exemplary tubing variant V1 comprises e.g. four valves and one pump 18, where two supply or discharge options 10, 21 exist there, which can each be connected to a port ZA1, ZA2 or ZA3 e.g. via valves, not shown. Exemplary tubing variant V2 allows for three supply or discharge options 22, 23, 24 which are each connectable to a port ZA1, ZA2 or ZA3, for example via valves, not shown.

In FIG. 15, PBE indicates a process influence, i.e. the possibility of selective process influencing and monitoring. For example, substances (products, sediments, raw, base and auxiliary materials, like hop products, such as umbels, oils, extracts, pellets, wood chips, enzymes, stabilizers, trub, yeast, other organisms, flavors, flavoring or coloring substances, substrate, fruit and fruit products, etc.) can be added and/or removed upstream and/or downstream of pump 18. In addition, physical influences, such as gasification and degassing of air, carbon dioxide, steam and/or nitrogen, tempering and/or separation/squeezing, solid deposits, can be performed e.g. with the aid of filters, centrifuges, hydrocyclones, decanters, press screws, etc. The type of pump employed should be adapted to the process in dependence of the requirements and can optionally also be adapted in terms of capacity (for example, by way of a frequency controller). Connecting pump 18 to other measuring and control technology, which can be located e.g. in the fermentation tank and/or at other process points (e.g., density measurements, flow and/or filling level measurement), is possible and useful.

Figure 16:
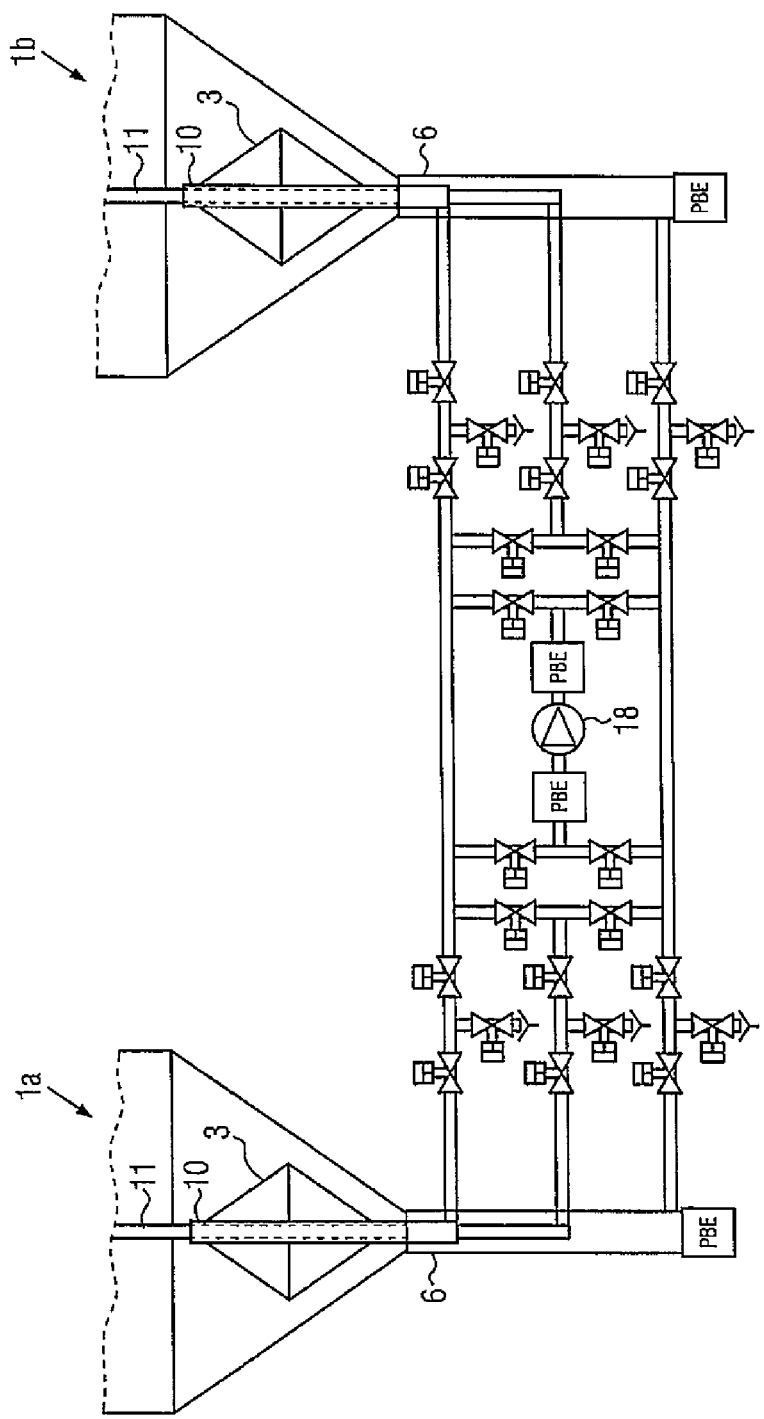
FIG. 16 shows two fermentation tanks connected to each other.

It is also possible to interconnect several reactors. A fermentation tank is there connected to at least one further fermentation tank such that, in particular, first supply or discharge line 6 of a tank 1a can be connected to a first supply or discharge line 6 of a second tank 1b, as is apparent, for example, in FIGS. 16-19. Preferably, second and/or third supply line 10, 11 of a first tank 1a is respectively connectable to second and/or third supply or discharge line 10, 11 of a further tank 1b, as is apparent, in particular, in FIG. 16. In principle, however, any combination of all inlets and outlets of upstream and downstream tanks (i.e. first and/or second and/or third supply/discharge line) is possible, even if this is not shown in FIGS. 18 and 19. In addition to fixed tubing, however, also mobile stations and/or flexible solutions, such as hoses, can be used to realize the method according to the invention in several tanks or to combine them with one another. The fermentation tank according to the invention is particularly suitable for continuous process management, as shall be explained in more detail in the context of FIGS. 17-19. This means that the device according to the invention is suitable not only for conventional batch operation but can also be used for semi-continuous and fully continuous operation, each with or without circulation. In this case, individually adjustable circulation can take place in each fermentation tank 1, where sediments can nevertheless deposit selectively, depending on the operation, where they can also be selectively extracted and supplied to the process elsewhere. In addition, separation processes can be promoted by the circulation By cascading several tanks, fractionation of particles, gases and fluids can be realized. Forwarding is then effected, for example, by way of pump(s) 18 and/or due to pressure gradients.

Figure 17:
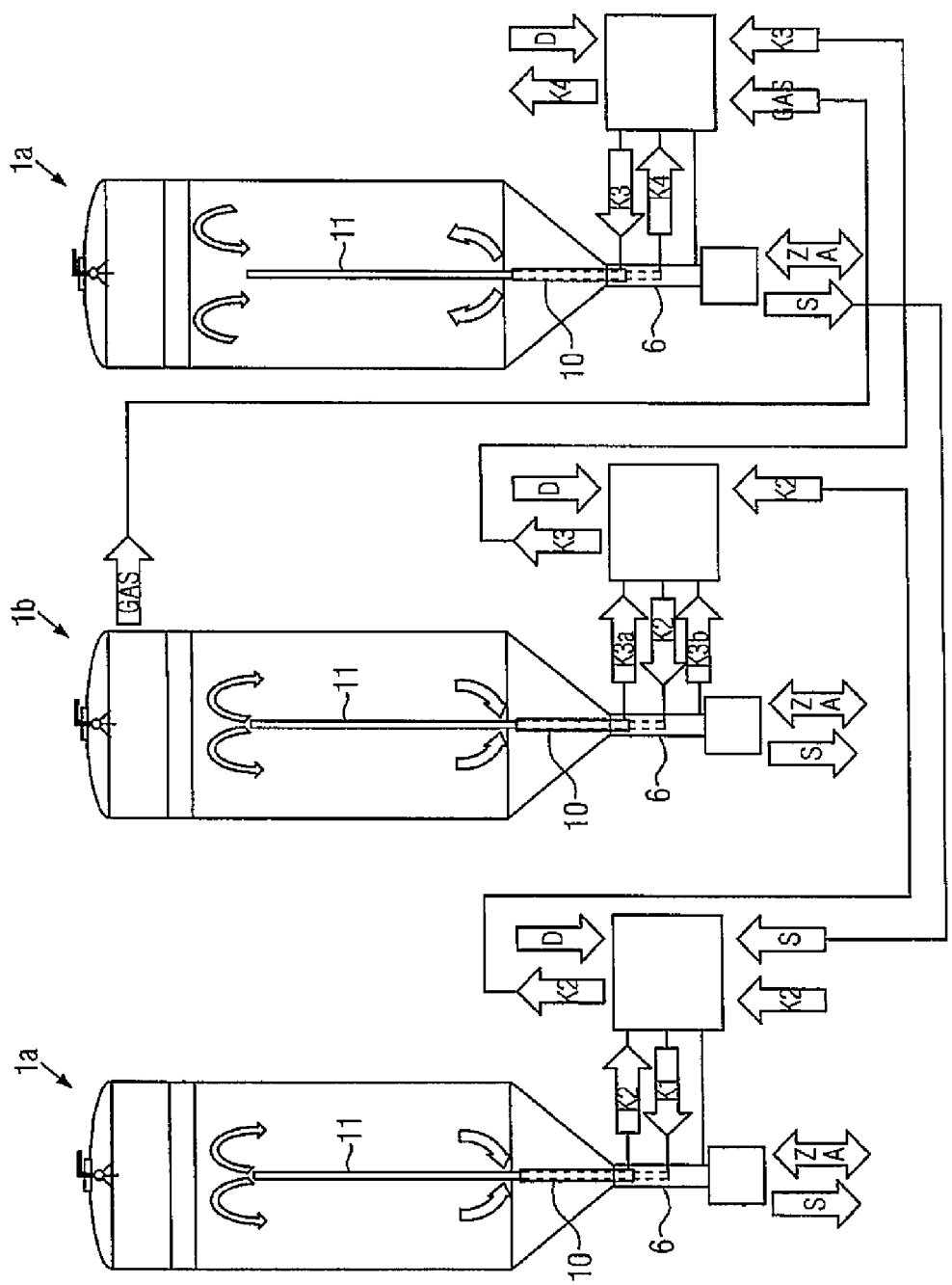
FIG. 17 shows three fermentation tanks interconnected in series.

For example, FIG. 17 shows three interconnected tanks. Paths K1-K4 indicate a possible flow through the cascade of tanks. K3a and K3b show variants of extraction from the tank Additional supplies and discharges are possible via supply and discharge ports ZA. D represents a dosage or further supply option, e.g. krausen in beer fermentation. Sediments S can be extracted and reused. Gas can be extracted from the tanks and e.g. be reused for gas scrubbing in the same and/or a further tank.

Figure 18:
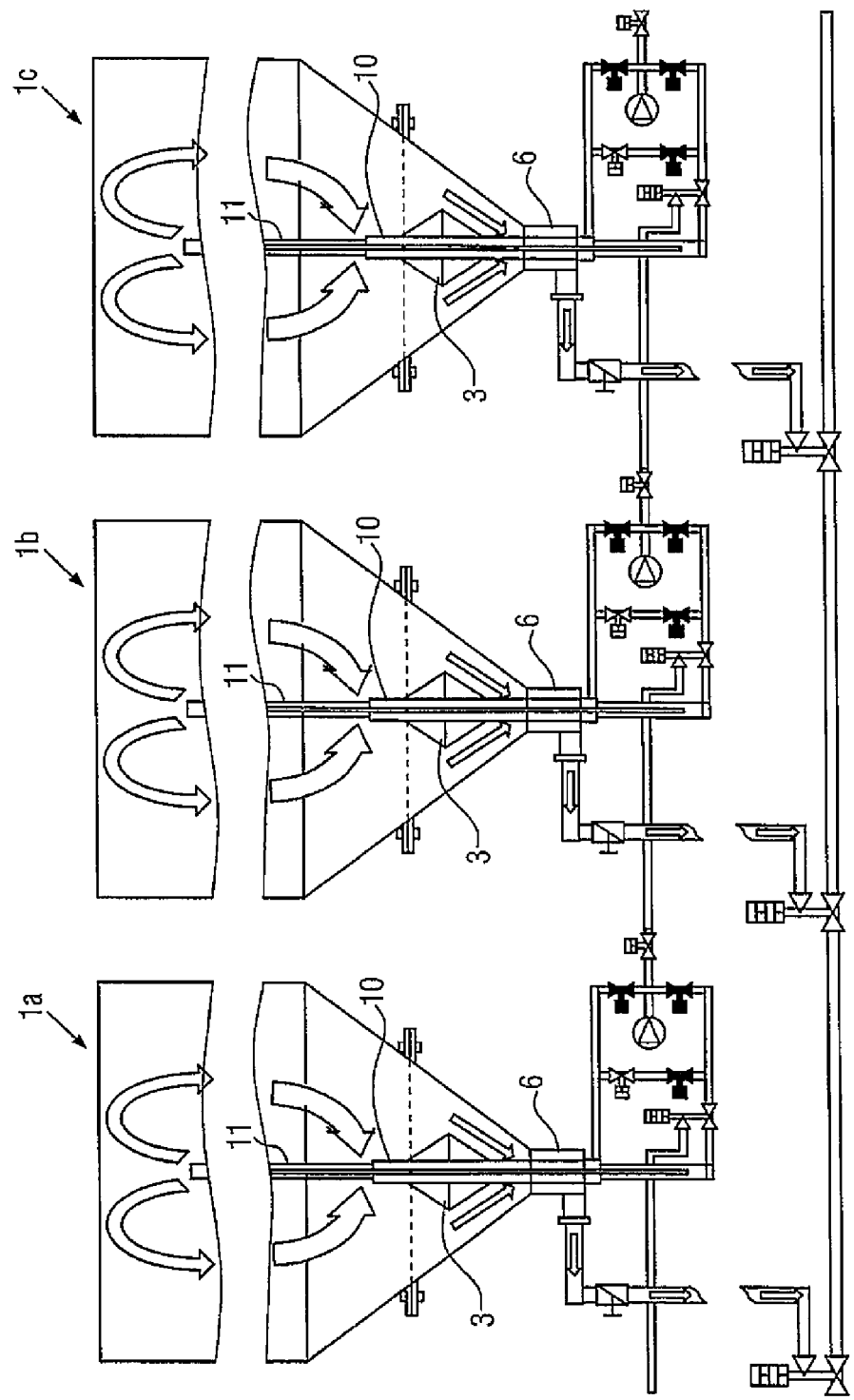
FIG. 18 shows three fermentation tanks interconnected in series for continuous operation.
Figure 19:
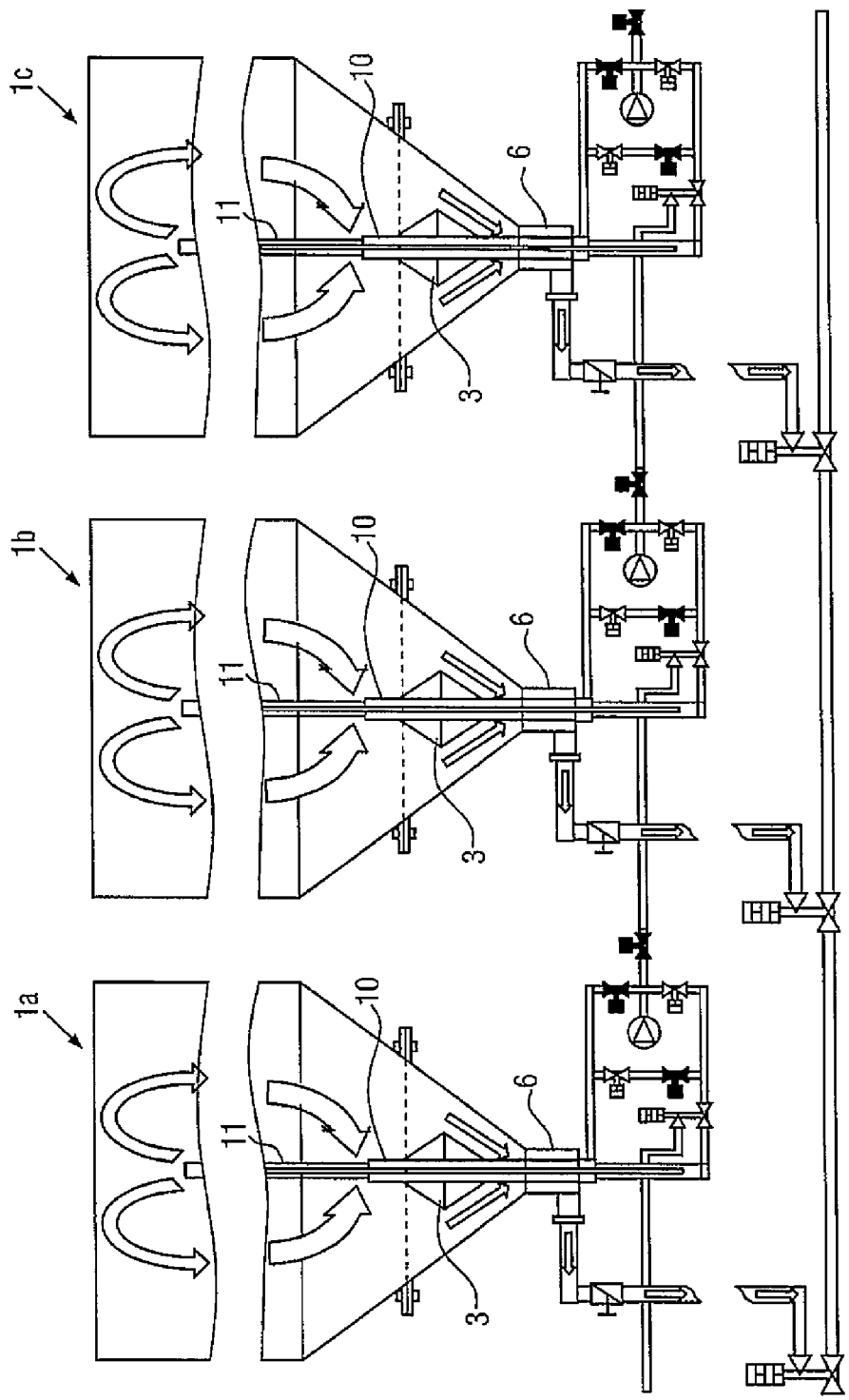
FIG. 19 shows the illustration shown in FIG. 18 in batch mode.

FIGS. 18 and 19 show tubing variants, how, for example, three tanks 1a, b, c can be interconnected.

For semi or fully continuous operation of interconnected tanks according to the invention, it is particularly advantageous if a pressure gradient in the cascade is set such that at least one of the upstream tanks has a higher pressure than at least one of the downstream tanks. According to the invention, a fluid transfer can then be ensured without additional pumps. A control valve is ideally also disposed between the tanks and is opened when the filling level in the downstream tank drops. With such an interconnection, semi- or fully continuous liquid transfer can be easily realized and the particles can nevertheless be selectively segmented, deposited and optionally further processed in individual systems or reused, respectively, due to the variably mixable zones. By using pressure gradients and control valves which are controlled by filling level measurements, the flow through a cascade can be easily controlled by the amount of liquid supplied or discharged and the costs of transfer pumps, measurement and control technology can be reduced.

FIG. 18 shows a possible interconnection for continuous operation of the cascade of tanks, where e.g. the valves in black are presently closed. Therefore, it becomes clear that e.g. product can presently be passed through opening 10a of second supply or discharge line 10 to the respective next tank, as already explained above. The valves are switched in FIG. 19 such that the cascade of tanks is operated in batch mode and no product is passed via first and second supply or discharge line 10, 11 to downstream tank 1b.

Figure 20A:
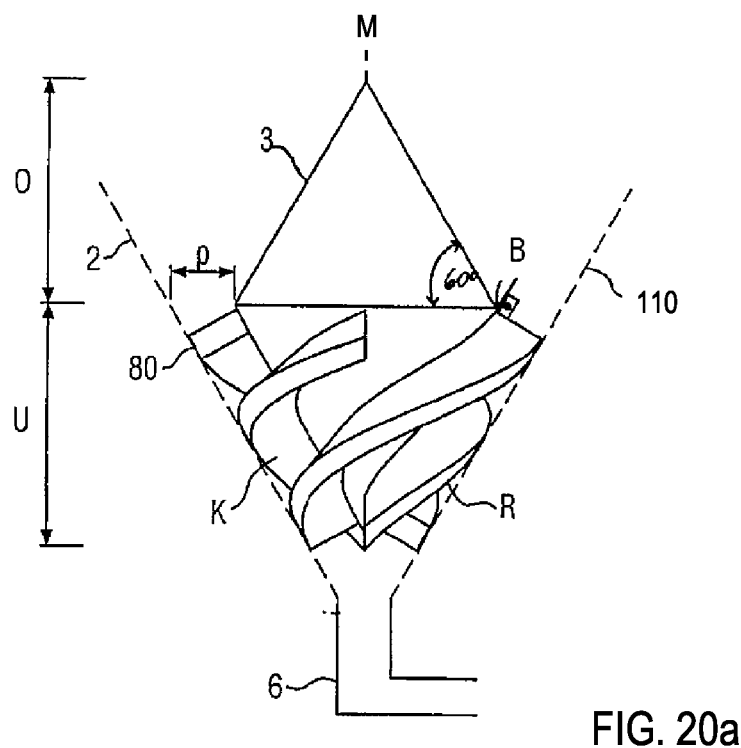
FIG. 20*a* shows an embodiment of a displacement member according to the invention in a perspective view.
Figure 20B:
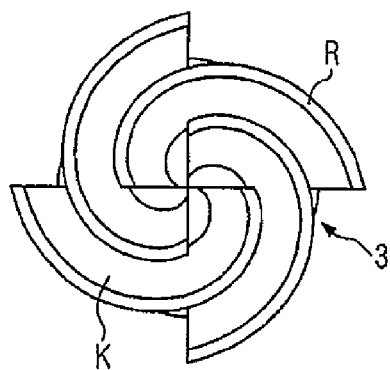
FIG. 20*b* shows a view from below onto the displacement member of FIG. 20*a*.
Figure 21A:
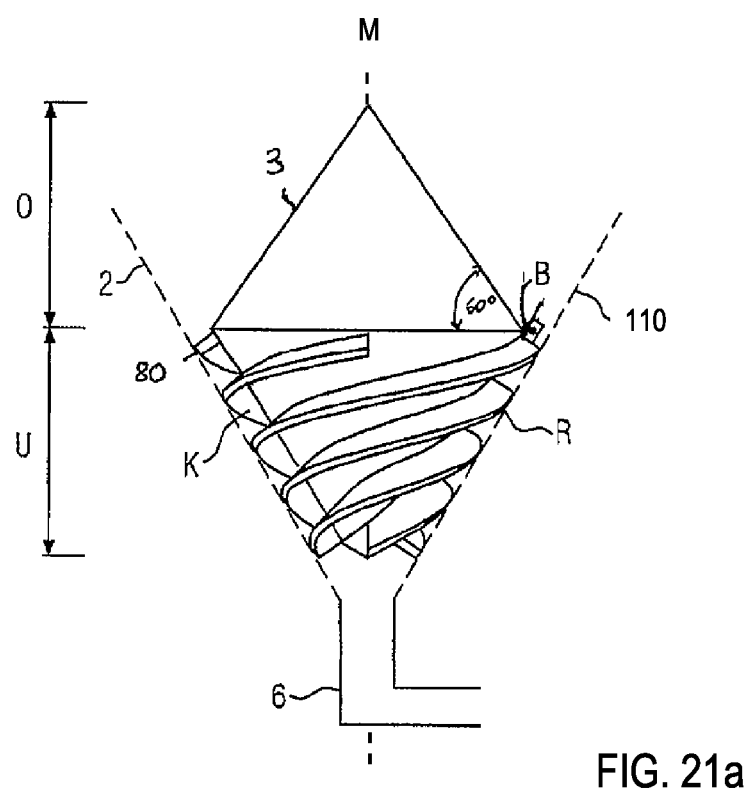
FIG. 21*a* shows a further embodiment of a displacement member according to the invention in a perspective view.
Figure 21B:
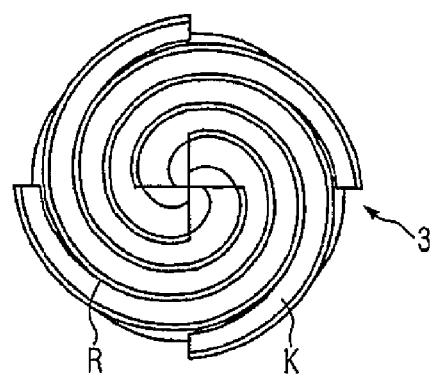
FIG. 21*b* shows a view from below onto the displacement member of FIG. 21*a*.

FIG. 20a shows a perspective representation of a displacement member 3 according to a preferred embodiment which is presently used in a conical lower tank region 2. Member 3 comprises a lower conical region (denoted by U) and an upper region (denoted by O) tapering upwardly. The taper angle of the lower region preferably corresponds to the taper angle of the lower tank region, e.g. 60°, distance p (viewed in the horizontal direction or perpendicular to the longitudinal axis) between the tank and the displacement member in the lower region of the displacement member is then substantially constant. The upper side can be formed e.g. to be smooth. The lower cone region of the displacement member 3 is configured such that a rotational motion of the product can be caused during filling, emptying and/or circulation. For this purpose, the lower region has a plurality of elevations R, presently in the form of ribs, which spiral about center axis M of the displacement member. In the embodiment illustrated in FIGS. 20a, b, there are four spiraled ribs, each of which spirals around the lower tapered region of displacement member 3, for example by an angular range of 180°. Ribs R are mounted on the lower tapered region e.g. at an angle of 90°. This means that the lateral rib surfaces on an unwound tapered surface are disposed at an angle of 90° on the unwound tapered surface. As is evident from FIGS. 20a and 21a, respectively, it is then true that at each reference point B at which the rib surface contacts the tapered surface, a perpendicular to a straight line passing through B and the cone tip is disposed in the rib surface. However, this is just a preferred embodiment. It is advantageous if the ribs R, that spiral around the tapered surface of displacement member 3, bear with their outer surface or edge 80 against tank inner surface 110. Several outlet channels K can be created spiraled around the circumference of displacement member 3, each of which is defined by the tank inner surface 110, the surface of the displacement member and oppositely disposed lateral ribs. A corresponding displacement member can easily be inserted into and welded to the tapered lower tank region. The displacement member can be easily attached in this manner and also be retrofitted into existing systems. FIG. 20a, b is only an example. Depending on the size of displacement member 3 and the desired process influences, however, ribs R can have a more or less pronounced degree of spiraling, as shown, for example, in FIGS. 21a, b, where e.g. four ribs spiral by 360° about the center axis of displacement member 3. More or fewer ribs R can also be provided. Three to six ribs, preferably three to four ribs, can be provided. The angle at which the respective rib is placed onto the tapered surface can also vary, e.g. between 60°-120°. It is also possible that the upper tapered surface of displacement member 3 comprises ribs which cause the product to perform a rotational motion. As already described above, one or more lines can be passed through the displacement member.

The invention claimed is:

1. A fermentation tank comprising:
   a first supply or discharge line with a first central opening arranged at a bottom of said fermentation tank for supplying or discharging product in a form of wort laden with yeast or beer,
   a second and a third supply or discharge line each comprising a centrally disposed opening for supplying or discharging product, where
   said three openings are arranged at different height levels ($N_1$, $N_2$, $N_3$), wherein
   said first supply or discharge line comprises a first tube,
   said second supply or discharge line comprises a second tube and
   said third supply or discharge line comprises a third tube, said second and said third tube extending at least in sections within said fermentation tank,
   wherein said second and said third tube engage the interior of the tank by one of projecting from below through said first opening into the interior of said tank;
   projecting from above into the interior of said tank; or
   said second tube protrudes into the interior of said tank from below and said third tube from above,
   wherein said fermentation tank comprises tubing with a valve arrangement (V1, V2) which is configured such that at least one of
   circulation between the opening at the middle level ($N_2$) and the opening at the highest level ($N_3$) is possible, or
   circulation between the opening at the lowest level ($N_1$) and the opening at the middle level ($N_2$) is possible, said third tube arranged within said second tube, and wherein the inner, third tube projects beyond the outer, second tube.

2. The fermentation tank according to claim 1 and a displacement member being arranged in a lower tank region.

3. The fermentation tank according to claim 1, at least one of the height, the diameter, or the cross-sectional shape of at least one of said second or said tube is variable, and at least one of said second or said third tube being exchangeable at least in sections.

4. The fermentation tank according to claim 1, said fermentation tank comprises tubing with a valve arrangement (V1, V2) which is configured such that
   circulation between an opening at the highest level ($N_3$) and an opening at the lowest level ($N_1$) is possible.

5. The fermentation tank according to claim 1, and one or more flow guide devices adjoin at the end region of one or more of said second or said third tube or above one or more of said second or said third tube, the flow guide devices including at least one device selected from a group consisting of:
   a tube section that one of expands or tapes in cross-section, a plate-shaped distributor, a nozzle, a Venturi nozzle, a spray ball, a jet cleaner, a swirl element, a displacement member, and one or more distributor elements.

6. The fermentation tank according to claim 1, said tank being interconnected with at least one further tank, in which at least one of said first, second, or third supply or discharge line of a first tank is connectable to at least one of said first, second, third supply or discharge line of a second tank, where said first supply or discharge line of a first tank.

7. The fermentation tank according to claim 1, said fermentation tank being interconnected with at least one further fermentation tank and at least one of said second or said third supply or discharge line is each interconnectable with at least one of a second or a third supply or discharge line of a further tank.

8. The fermentation tank according to claim 1, said tank being connected to a dosage device, where a medium, can be added via at least one of said supply or discharge lines.

9. The fermentation tank of claim 1 wherein the second and third tube are arranged concentrically.

10. The fermentation tank of claim 2, wherein the displacement member is installed on at least one of the second or third tube.

\* \* \* \* \*